United States Patent [19]

Chiang

[11] Patent Number: 5,229,129
[45] Date of Patent: Jul. 20, 1993

[54] TRANSDERMAL ADMINISTRATION OF LISURIDE

[75] Inventor: Chia-Ming Chiang, Foster City, Calif.

[73] Assignee: Cygnus Therapeutic Systems, Redwood City, Calif.

[21] Appl. No.: 773,245

[22] Filed: Oct. 9, 1991

Related U.S. Application Data

[62] Division of Ser. No. 379,000, Jul. 12, 1989.

[51] Int. Cl.$^5$ ............................................. A61F 13/00
[52] U.S. Cl. ..................................... 424/449; 424/448; 514/946; 514/947
[58] Field of Search ................ 424/449, 448; 514/946, 514/947

[56] References Cited

U.S. PATENT DOCUMENTS

| | | | |
|---|---|---|---|
| 3,681,497 | 8/1972 | Semonsky et al. | 424/461 |
| 3,953,354 | 4/1976 | Faust et al. | 252/187 H |
| 3,954,988 | 5/1976 | Itil et al. | 424/261 |
| 4,692,452 | 9/1987 | Cerny | 514/288 |
| 4,731,367 | 3/1988 | Sauer | 514/288 |
| 4,764,379 | 8/1988 | Sanders | 424/449 |
| 4,826,851 | 5/1989 | Huth | 514/288 |
| 4,826,852 | 5/1989 | Haffer | 514/288 |
| 4,837,027 | 6/1989 | Lee | 424/449 |
| 4,973,468 | 11/1990 | Chiang | 424/449 |
| 5,071,657 | 12/1991 | Oloff | 424/486 |

Primary Examiner—Thurman K. Page
Assistant Examiner—D. Gabrielle Phelan
Attorney, Agent, or Firm—Morrison & Foerster

[57] ABSTRACT

Method and laminated composite for administering lisuride transdermally to treat conditions such as Parkinson's disease. The composite comprises an impermeable backing layer and a reservoir layer containing lisuride and a permeation enhancer combined with a pressure-sensitive adhesive with the amounts of lisuride and enhancer being sufficient to cause the lisuride to pass through the skin at a rate in excess of about one mcg/cm$^2$/hr.

6 Claims, 1 Drawing Sheet

TRANSDERMAL ADMINISTRATION OF LISURIDE

This application is a division of application Ser. No. 07/379,000 filed, Jul. 12, 1989.

TECHNICAL FIELD

This invention relates to a device and method for administering the drug lisuride transdermally.

BACKGROUND

Lisuride (N-(D-6-methyl-8-isoergolenyl)-N',N'-diethylurea hydrogen maleate) is an ergot derivative. It has alternatively been called ergoline. Lisuride is a serotonin antagonist and has also been reported to be a dopamine agonist. U.S. Pat. No. 3,953,454 describes the preparation of lisuride and its oral administration to animals as an antilactation agent. U.S. Pat. No. 3,681,497 describes its oral administration as a serotonin antagonist to treat migraine headache, urticaria, hypertension, and allergic conditions. U.S. Pat. No. 3,954,988 describes the administration of lisuride orally, by injection, or as an intramuscular depot as a psychic energizer.

U.S. Pat. No. 4,692,452 teaches the treatment of endometritis with lisuride. The patent indicates the drug may be administered orally or by injection. It also postulates that the drug can be administered transdermally through the application of ointments, creams or solutions prepared by combining lisuride with known carriers. No example of transdermal administration is given, and no data relating to the flux of lisuride through the skin are provided. Therefore, at best, this is a speculative teaching that leaves the reader with the task of experimenting to find out whether it is possible to administer lisuride transdermally in vivo at therapeutically effective rates.

Lisuride has also been administered subcutaneously using infusion pumps to reduce on-off motor response fluctuation in Parkinson's patients. J Neural Transm (1988) Suppl 27:85-90. The pharmacokinetics of lisuride following subcutaneous infusion are reported in J Neural Transm (1988) Suppl 27:71-74. For these Parkinson's patients, a constant subcutaneous infusion of 60 micrograms per hour for 12 hours resulted in a mean steady-state plasma level of 0.78±0.19 ng/ml with a range of 0.54 to 1.07 ng/ml.

Numerous patents and publications describe the use of various compounds as skin permeation enhancers. For instance, the use of propylene glycol monolaurate as a permeation enhancer for estradiol and other drugs is described in EPA 874029457.

The present invention is directed to achieving noninvasive sustained administration of lisuride at a controlled rate by delivering it, in combination with a skin permeation enhancer, transdermally from a laminated composite patch affixed to the patient's skin.

DISCLOSURE OF THE INVENTION

Accordingly, one aspect of the invention is a method for providing lisuride therapy to an individual in need of such therapy comprising administering a therapeutically effective amount of lisuride to the individual transdermally through a predetermined area of skin over a sustained time period at a controlled rate concurrently or sequentially in combination with a sufficient amount of a permeation enhancer to enable the lisuride to permeate the area of skin at a rate in excess of about one microgram per $cm^2$ of skin per hour.

Another aspect of the invention is a laminated composite for administering lisuride to an individual transdermally through a predetermined area of skin of the individual comprising:

a) a backing layer that is substantially impermeable to lisuride; and b) a reservoir layer comprising a pressure-sensitive adhesive polymer, lisuride dissolved in said polymer, and a permeation enhancer that increases the permeability of the skin to lisuride dissolved in said polymer, the basal surface of said reservoir layer being adapted to be adhered to said area of skin and wherein the amounts of lisuride and enhancer in said reservoir layer are sufficient to enable a therapeutically effective amount of lisuride to be administered at a rate in excess of about one microgram per $cm^2$ of skin per hour to the individual through said predetermined area of skin over a sustained time period.

BRIEF DESCRIPTION OF THE DRAWING

The drawing shows an embodiment of a skin patch for administering lisuride free base transdermally.

MODES FOR CARRYING OUT THE INVENTION

Figure 1:
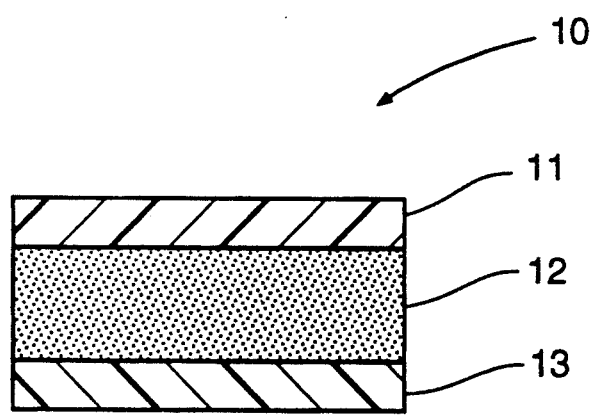

As used herein the term "transdermal" intends both percutaneous and transmucosal administration, i.e., passage of lisuride through intact unbroken skin or mucosal tissue into circulation.

As used herein the term "lisuride therapy" means those medical conditions for which lisuride is or will be indicated, including, without limitation, as a psychic energizer and in the treatment of Parkinson's disease, migraine, allergic responses, urticaria, hypertension, endometritis, and other conditions associated with serotonin excess.

As used herein the term "individual" intends a living mammal and includes, without limitation, humans and other primates, livestock and sports animals such as cattle, pigs and horses, and pets such as cats and dogs.

As used herein the term "therapeutically effective amount" intends that dose of lisuride that provides lisuride therapy. In the case of adult humans, the dose is normally in the range of about 1-2 mg per day.

As used herein the phrase "sustained time period" means at least about one day and will typically intend a period in the range of about 1 to about 7 days.

As used herein the phrase "predetermined area of skin" intends a defined area of intact unbroken living skin or mucosal tissue. That area will usually be in the range of about 5 $cm^2$ to about 100 $cm^2$.

As used herein the term "controlled rate" intends a time course of lisuride administration to circulation that is predetermined and governed by the area of skin through which the drug is passed, the permeability of the skin to the drug, and the activity of the drug maintained in the laminated composite over the duration of administration.

"Permeation enhancement" as used herein relates to an increase in the permeability of skin to lisuride as compared to the permeability of skin to lisuride as measured by the diffusion cell apparatus described in the examples using lisuride formulated in aqueous phosphate buffer, pH 7, as a baseline.

Based on the subcutaneous infusion studies done on Parkinson's patients, applicant estimated that skin fluxes in the range of 1-2 mcg/cm$^2$/hr would be required to deliver therapeutically effective amounts of lisuride transdermally through a practical skin area (i.e., less than about 100 cm$^2$). However, when applicant measured the in vitro flux of lisuride through skin from aqueous phosphate buffer solutions, she found the flux at optimum pH was more than an order of magnitude less than the flux required to deliver a therapeutic amount of the drug through such an area of skin. Applicant thus attempted to enhance the flux of the drug through skin by administering it from various nonaqueous media and surprisingly found that the skin flux could be increased up to fifty-fold by formulating the drug with certain nonaqueous carriers. This finding enabled applicant to develop laminated composites that permit lisuride to be administered transdermally through a practical area of skin at rates that result in plasma levels of the drug that provide desired therapeutic effects.

A preferred laminated composite for administering lisuride free base transdermally to humans to reduce on-off motor response fluctuation in Parkinson's patients is shown in the drawing. This composite, generally designated 10, comprises a backing lamina 11, a reservoir lamina 12, and a release liner lamina 13.

The backing layer provides a protective covering for the composite and may itself be a single layer or a multiplicity of layers. For instance if the composite is to be worn for periods in excess of a day or two, it is desirable to make the backing from an elastomeric polymer such as polyurethane, polyether amide, and copolyester. In order to insure the occlusiveness of such elastomeric polymers, it may be necessary to place a layer of an occlusive material such as polyisobutene between the backing and the reservoir. For devices that are intended to be worn for shorter durations, the backing may be made from relatively flexible but not elastomeric occlusive polymers such as polyester, polyethylene, and polypropylene. The thickness of the backing layer will normally be in the range of about 15 microns to about 250 microns.

The reservoir lamina is composed of lisuride, a nonaqueous vehicle/permeation enhancer, and a hydrophobic pressure-sensitive adhesive polymer. The lisuride is present in the layer in excess of its solubility in the two other components. It will normally constitute about 1% to about 10% by weight of the lamina. The nonaqueous vehicle/enhancer is present in the layer in amounts ranging between about 2 to about 20% by weight. Preferred enhancers are esters of the formula $[CH_3(CH_2)_mCOO]_nR$ in which m is an integer from 8 to 16, preferably 8 to 12, most preferably 10; n is 1 or 2, preferably 1; and R is a lower alkyl ($C_1$-$C_3$) residue which may be substituted with 0 to 2 hydroxyl groups, or a mixture of such an ester or methyl laurate and diethylene glycol monomethyl or monoethyl ether. The volume ratio of ester to ether in such mixtures will normally be in the range of 90:10 to 50:50. The use of such mixtures as permeation enhancers is described in commonly owned copending U.S. Pat. application Ser. No. 327312, filed 22 Mar. 1989. The preferred esters of the above formula are lower alkyl ($C_1$-$C_3$) esters of lauric acid, with propylene glycol monolaurate (PGML) being particularly preferred. It will be appreciated by those skilled in the art that commercially available PGML is normally a mixture of propylene glycol monolaurate, propylene glycol dilaurate and either propylene glycol or methyl laurate or both. Thus "propylene glycol monolaurate" is intended to encompass the pure compound as well as the mixture that is sold commercially. It is also intended that the enhancer may be composed of a mixture of said esters, by themselves or in combination, one or both of the mentioned ethers.

The third component of the reservoir is a hydrophobic pressure-sensitive adhesive such as a silicone or acrylate adhesive. A tackifier, such as silicone oil in the case of silicone adhesive, may be included in the reservoir formulation. The thickness of the reservoir layer will normally be in the range of 20 microns to 150 microns, preferably 25 microns to 100 microns.

The reservoir lamina plays two functional roles, namely, it is a reservoir for lisuride and the solvent/enhancer, and because of its composition, it is adhesive and its basal surface provides the means by which the composite is affixed to the skin. The basal release liner lamina 13 is a protective coating for the reservoir lamina during storage and prior to affixation to the skin. This layer is removed from the composite before the composite is affixed to the skin.

The reservoir layer may be formulated by conventional methods known in the field of transdermal drug delivery devices and the three layers assembled into a laminated composite by like methods. These methods and specific embodiments of the invention are further illustrated by the following examples. These examples are not intended to limit the invention in any manner.

EXAMPLE 1

In Vitro Skin Flux of Lisuride from Various Vehicles Materials

Lisuride free base was obtained from Schering A. G. Diethylene glycol monoethyl ether (Transcutol) and propylene glycol monolaurate (PGML) were obtained from Gattefosse (Elmsford, N.Y.). Methyl laurate was obtained from Sigma (St. Louis, Mo.). All chemicals were reagent grade.

Skin Permeation Methodology

Human cadaver skin was used for in vitro permeation studies. Frozen skins were thawed and epidermal layers (stratum corneum and viable epidermis) were separated from the full-thickness skin by immersion in water at 60° C. for 2 minutes. This epidermis was either used immediately for diffusion studies or stored at −20° C. for later studies.

The skin sections were mounted carefully between the two halves of a side-by-side diffusion cell in the case of aqueous lisuride formulations or a modified Franz cell in the case of the nonaqueous formulations. The receiver compartment was filled with 5 ml of pH 6 phosphate buffer. The experiment was initiated by placing test lisuride formulation (5 ml for aqueous, 200 ul for nonaqueous) in the donor compartment. The diffusion/Franz cells were placed in an incubator at 32° C. At pre-determined times, a 1 ml aliquot was withdrawn from the receiver and replaced with fresh buffer. Samples were assayed by HPLC using UV-detection at 241 nm. Adequate chromatographic resolution was achieved using a Supelco LC-18 DB column. The mobile phase was acetonitrile-water (35:65) with 0.3 ml diethylamine per liter. The retention time was about 8-9 min.

Skin flux (ug/cm$^2$/hr) was determined from the steady-state slope of a plot of the cumulative amount of lisuride permeated through the skin versus time.

Results

The permeation of lisuride from saturated aqueous buffers through cadaver skin at 32° C. is presented in Table 1. The pH used for the donor media ranged from 6-8 since extreme pHs such as pH 3 or 9 may damage the skin membrane and, therefore, affect the permeation.

TABLE 1

| pH | % free base | Solubility (ug/ml) | Flux (ug/cm$^2$/hr) |
|---|---|---|---|
| 6 | 1.67 | 186.0 | 0.10 ± 0.04 |
| 7 | 14.5 | 22.8 | 0.09 ± 0.06 |
| 8 | 62.9 | 9.56 | 0.06 ± 0.01 |

The results show that the flux of lisuride from these buffers is approximately 0.05–0.10 ug/cm$^2$/hr.

The permeation of lisuride free base from various saturated nonaqueous vehicles (PGML, methyl laurate (ML), diethylene glycol monoethyl ether (Transcutol or "TC"), TC:PGML mixtures) through cadaver skin and TC:ML mixtures is presented in Table 2 below.

TABLE 2

| Vehicle | Flux (ug/cm$^2$/hr) Mean ± SD (n = 3) |
|---|---|
| PGML | 2.80 ± 0.14 |
| TC:PGML (10:90) | 3.39 ± 0.36 |
| TC:PGML (20:80) | 4.94 ± 0.23 |
| TC:PGML (50:50) | 3.04 ± 0.47 |
| TC:PGML (80:20) | 0.81 ± 0.10 |
| TC | 0.25 ± 0.15 |
| TC:ML (20:80) | 3.12 ± 0.01 |
| TC:ML (50:50) | 1.68 ± 0.17 |
| TC:ML (80:20) | 1.11 ± 0.07 |
| ML | 0.47 ± 0.15 |

The maximal lisuride flux in these experiments was obtained with a 20:80 ratio of TC and PGML. Lisuride flux decreased as the % of TC increased over 20%. The same trend was observed for the combination of TC and ML. The flux of lisuride from PGML is much higher than from ML or TC alone.

In Vitro Skin Flux of Lisuride from Laminated Composites

Two types of prototype laminated composite were prepared by the following method. Two percent of lisuride free base was mixed with vehicle (15% PGML or 20% TC with PGML (20:80)) and sonicated for 10 minutes. An appropriate amount of silicone adhesive (Silicone #2675, Dow Corning) was then added to the mixture. The resulting drug/vehicle/silicone mixture was rotated overnight. A 75 micron thick drug reservoir lamina was made by laminating the mixture on a polyester release liner (3M #1022) with an 8 mil knife. The solvent in the polymer was removed by heating the polymer matrix in an oven at 70° C. for 20 minutes to yield the first type of prototype. The second type of prototype composite was made by laminating the drug polymer matrix with a 75 micron thick intermediate polyisobutylene layer, then overlayering the polyisobutylene with a polymer elastomer (PBAX 810, Bertek; Polyurethane 810, 3M). Lisuride flux from the prototypes was measured as described previously. The prototype systems were peeled from the polyester release liner and placed on top of the epidermis with the drug adhesive layer facing the stratum corneum. Gentle pressure was applied to insure full contact between the bond surface of the reservoir layer and stratum corneum. The skin membrane with the prototype was then mounted carefully between the donor and the receiver compartments. The results of these tests are summarized in Table 3 below.

TABLE 3

| Prototype System | Flux (ug/cm$^2$/hr) Mean ± SD (n = 3) |
|---|---|
| Lisuride/TC:PGML/Silicone (Type 1) | 1.35 ± 0.12 |
| Lisuride/TC:PGML/Silicone (Type 2) | 1.79 ± 0.28 |
| Lisuride/PGML/Silicone (Type 1) | 1.46 ± 0.08 |
| Lisuride/PGML/Silicone (Type 2) | 1.10 ± 0.18 |

The flux of lisuride from the type 1 prototype made with PGML was 1.46±0.08 ug/cm$^2$/hr, while the flux of lisuride from the corresponding type 2 prototype was 1.10±0.18 ug/cm$^2$/hr. The flux decreased as the polyisobutylene layer and polymer elastomer were laminated on the drug reservoir. This could be due to the diffusion of PGML into the added layers. The flux of lisuride from the type 1 design made with TC and PGML was 1.35±0.12 ug/cm$^2$/hr while the flux of lisuride from the type 2 proto-type design was 1.79±0.28 ug/cm$^2$/hr. These results suggest that the combination vehicles were not taken up into the added layers as was PGML, and therefore the delivery rates for the two prototypes were quite similar. Based on these data, it is clear that a constant delivery rate of lisuride through human cadaver skin was obtained.

Modifications of the above-described modes for carrying out the invention that are obvious to those of skill in the field of transdermal drug delivery devices are intended to be within the scope of the following claims. For instance the permeation enhancer could be administered to the skin prior to the administration of lisuride. Such sequential administration would be equivalent to the concurrent administration described above.

I claim:

1. A laminated composite for administering lisuride to an individual transdermally through a predetermined area of skin comprising:

a) a backing layer that is substantially impermeable to lisuride; and b) a nonaqueous reservoir layer comprising a pressure-sensitive adhesive polymer, lisuride dissolved in said polymer, and a permeation enhancer that increases the permeability of the skin to lisuride dissolved in said polymer, the basal surface of said reservoir layer being adapted to be adhered to said area of skin and wherein the amounts of lisuride and enhancer in said reservoir layer are sufficient to enable about 1 to 2 mg/day of lisuride to be administered at a rate in excess of about one microgram per cm$^2$ of skin per hour to the individual through said predetermined area of skin for at least about one day.

2. The laminated composite of claim 1 wherein the enhancer is an ester of the formula $$[CH_3(CH_2)_mCOO]_nR$$

wherein m is an integer from 8 to 16, n is 1 or 2 and R is alkyl of 1 to 3 carbon atoms, a mixture of said ester and diethylene glycol monomethyl or monoethyl ether, or a mixture of methyl laurate and diethylene glycol monomethyl or monoethyl ether.

3. The laminated composite of claim 1 wherein the enhancer is propylene glycol monolaurate or a mixture of diethylene glycol monoethyl ether and propylene glycol monolaurate.

4. The laminated composite of claim 3 wherein the volume ratio of said monolaurate to said ether is in the range of about 90:10 and 50:50.

5. The laminated composite of claim 1 wherein the pressure-sensitive adhesive is a silicone adhesive.

6. The laminated composite of claim 1 wherein the lisuride constitutes 1 to 10% by weight of the reservoir lamina and the enhancer comprises 2 to 20% by weight of the reservoir layer.

* * * * *